United States Patent [19]
Matsunaga

[11] Patent Number: 5,861,285
[45] Date of Patent: Jan. 19, 1999

[54] FUSION PROTEIN-BOUND MAGNETIC PARTICLES FOR RECOMBINANT PRODUCTION AND MAGNETIC SEPARATION OF POLYPEPTIDES OF INTEREST

[75] Inventor: Tadashi Matsunaga, Fuchu, Japan

[73] Assignee: TDK Corporation, Tokyo, Japan; A part interest

[21] Appl. No.: 529,600

[22] Filed: Sep. 18, 1995

[30] Foreign Application Priority Data

Sep. 16, 1994 [JP] Japan ................................ 6-248700

[51] Int. Cl.[6] .......................... C12N 15/62; C07K 14/195
[52] U.S. Cl. .................. 435/69.7; 435/252.3; 435/320.1; 536/23.4; 536/23.7
[58] Field of Search ................................ 435/69.7, 252.3, 435/320.1; 536/23.4, 23.7; 530/427, 350

[56] References Cited

PUBLICATIONS

Matsunaga et al, "Gene Transfer in Magnetic Bacteria: Transposon Mutagenesis and Cloning of Genomic DNA Fragments Required for Masgnetosome Synthesis", Journal of Bacteriology, May 1992, pp. 2748–2753.

Nakamura et al, "Iron–Regulated Expression and Membrane Localization of the MagA Protein in *Magnetospirillum* sp. Strain AMB–1", *J. Biochem.*, 118, 23–27 (1995).

Nakamura et al, "An Iron–regulated Gene, magA, Encoding an Iron Transport Protein of *Magnetospirillum*sp. Strain AMB–1", *The Journal of Biological Chemistry*, vol. 270, No. 47, Nov. 24, 1995, pp. 28395–28396.

Nakamura et al, "Analysis of a Gene, magA, Required for Magnetite Biomineralization in the Bacterium *Magnetospirillum*sp. AMB–1", Biomineralization 93, 7th International Symposium on Biomineralization, Monaco –17–20 Nov. 1993, Monaco Musee Oceanographique 1995, pp. 121–126.

*Primary Examiner*—David L. Fitzgerald
*Attorney, Agent, or Firm*—Pillsbury Madison & Sutro LLP

[57] ABSTRACT

A fusion DNA sequence, which is obtained by fusing a gene coding for another useful protein to a fragment of a magA gene coding for a protein bound to an organic membrane for covering magnetic particles produced in cells of a magnetic bacterium AMB-1, is expressed in the magnetic bacterium to obtain the protein in a state of being bound to the magnetic particles. According to the present invention, useful proteins such as enzymes and antibodies can be stably obtained in a state of being bound to the organic membrane of the magnetic particles only by cultivating a transformed magnetic bacterium, and separating the magnetic particles produced in cells, without any necessity to perform a treatment such as immobilization. The functional protein immobilized on the magnetic particles can be magnetically controlled. Thus the function can be efficiently exhibited at a desired topical position. Magnetic particles to which a desired protein is bound can be semipermanently produced only by maintaining and cultivating an identical bacterial strain. Since the protein is produced on the magnetic particles, an objective protein can be magnetically separated and recovered in a short period of time. Thus it is possible to perform efficient separation and purification.

17 Claims, 10 Drawing Sheets

FUSION PROTEIN-BOUND MAGNETIC PARTICLES FOR RECOMBINANT PRODUCTION AND MAGNETIC SEPARATION OF POLYPEPTIDES OF INTEREST

BACKGROUND OF THE INVENTION

1. Field of the Invention

The present invention relates to protein-bound magnetic particles and a production method thereof, as well as a novel gene, gene fragment, fusion DNA sequence, recombinant plasmid, and transformed magnetic bacterium.

2. Description of the Prior Art

Proteins having biological activities such as enzymes and antibodies immobilized on magnetic particles can be led by magnetic means. Therefore, they can be led to local positions at which it has been hitherto difficult to arrive. Further, they can be collected and separated by using a magnetic force. Thus they are expected to be utilized in various industries including the fields of medicine and fermentation.

In the prior art, for example, immobilization of biologically active substances to magnetic particles is disclosed in Japanese Patent Publication (KOKOKU) No. 6-12994. Namely, magnetic particles are separated from a magnetic bacterium by an alkaline treatment, and they are treated with γ-aminopropyltriethoxysilane or glutaraldehyde, to which a biologically active substance is chemically immobilized. A method is also known, in which magnetic particles are separated by an enzyme treatment from a magnetic bacterium in a state of being covered with an organic thin membrane comprising lipid, and a protein is immobilized thereto after a treatment with glutaraldehyde. A method is also known, in which a biologically active substance is immobilized on magnetic particles by a chemical binding method by using SPDP (Japanese Pre-examination Patent Publication (KOKAI) No. 5-209884).

Further, methods for measuring antigens or antibodies have been proposed, in which an antigen-antibody reaction is performed by using the magnetic particles to which a biologically active substance is chemically immobilized by the aforementioned methods (Japanese Pre-examination Patent Publication (KOKAI) Nos. 4-285857, 5-209884, and 5-99926).

However, in any of the foregoing, it is necessary for a protein such as an enzyme, or an antibody, etc. to be chemically bound to magnetic particles. Thus problems have arisen in that a long period of time is required for the immobilization treatment, that the biological activity of the protein is deteriorated due to the immobilization treatment, that the amount of obtained immobilized protein is greatly dispersed among lots, that the activity is also greatly dispersed, and that the immobilized protein inevitably becomes expensive because the protein to be used for immobilization is generally expensive.

SUMMARY OF THE INVENTION

Accordingly it is a task of the present invention to provide protein-bound magnetic particles, etc. in which the aforementioned problems are solved.

According to a first aspect of the present invention, there is provided an isolated and purified magA gene which codes for a protein bound to an organic membrane for covering magnetic particles produced in cells of a magnetic bacterium AMB-1, and comprises a DNA sequence represented by SEQ ID NO: 1 defined in Sequence Listing.

In another aspect, the present invention provides an isolated and purified MagA protein which is a protein bound to an organic membrane for covering magnetic particles produced in cells of a magnetic bacterium AMB-1, and comprises an amino acid sequence represented by SEQ ID NO: 2 defined in Sequence Listing described below.

Taking notice of the property of the MagA protein to bind to the organic membrane for covering the magnetic particles produced in cells of the magnetic bacterium, the present invention provides a method for immobilizing another useful protein to the magnetic particles in a state of a fusion protein, a method for producing useful proteins on the magnetic particles, and so on.

According to the present invention, useful proteins such as enzymes and antibodies can be stably obtained in a state of being bound to the organic membrane of the magnetic particles only by cultivating a transformed magnetic bacterium, and separating the magnetic particles produced in cells, without any necessity to perform a treatment such as immobilization. When the useful protein is a functional protein, the functional protein immobilized on the magnetic particles can be magnetically controlled. Thus the function can be efficiently performed at a desired topical position.

Further, any protein can be produced on the magnetic particles by introducing a gene coding for a desired protein into a plasmid of the present invention, and transforming a magnetic bacterium.

It is unnecessary to prepare an expensive protein such as an enzyme and an antibody. Magnetic particles to which a desired protein has bound can be semipermanently produced only by maintaining and cultivating an identical bacterial strain. The protein content and the activity do not disperse among production lots, and there is a great merit of low cost. The magnetic particles thus obtained always contain the protein having an identical activity in an identical amount.

Further, since the protein is produced on the magnetic particles, an objective protein can be magnetically separated and recovered in a short period of time. Thus it is possible to perform efficient separation and purification.

Figure 1:
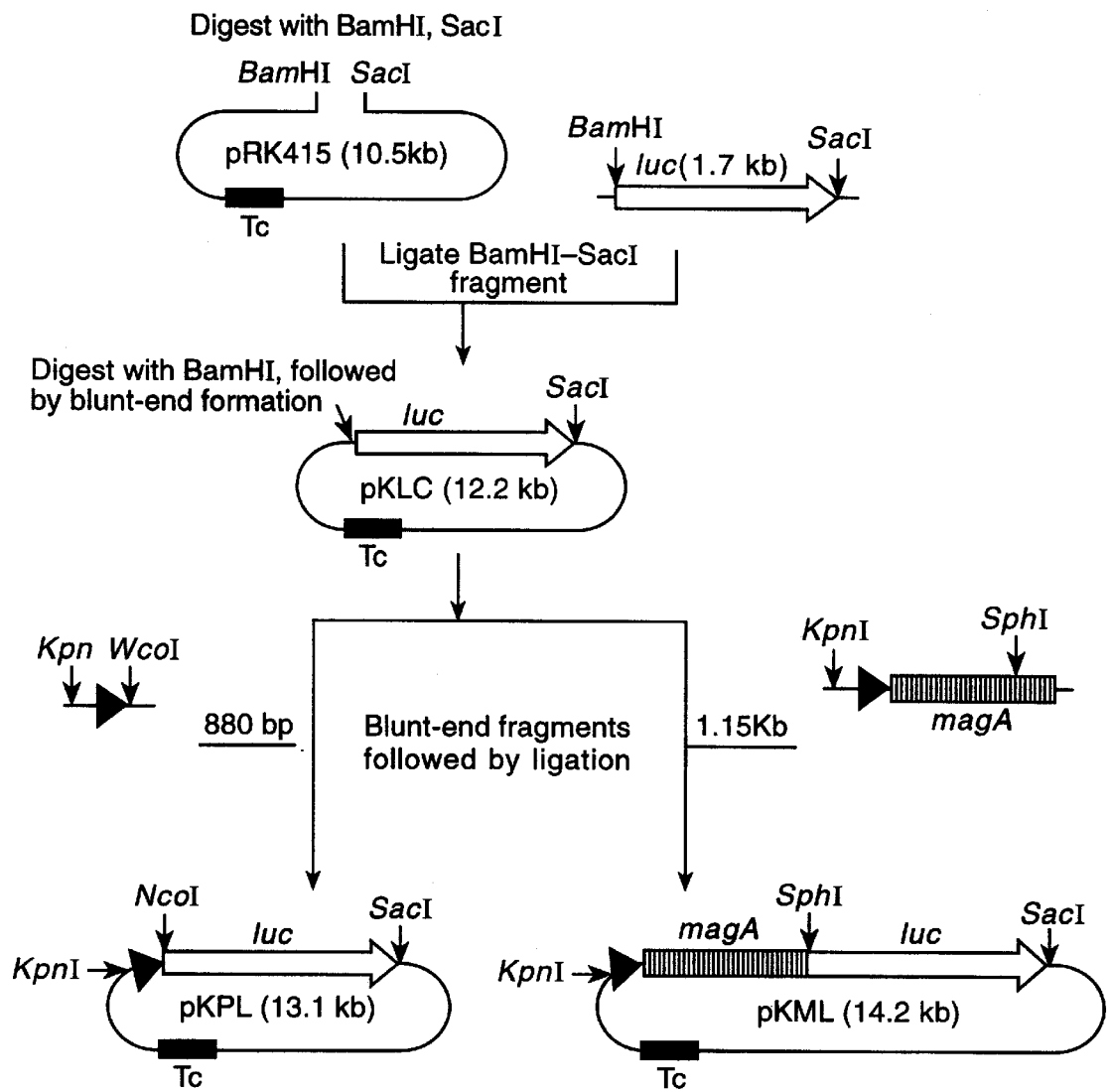
FIG. 1 is an explanatory view for a method for preparing plasmids pKPL and pKML prepared in Example 1.

DETAILED DESCRIPTION OF THE PREFERRED EMBODIMENTS magA gene

The present inventors have found the magA gene which comprises a DNA sequence represented by a base sequence as depicted by SEQ ID NO: 1 in Sequence Listing described below, and codes for a protein bound to an organic membrane containing phospholipid as a major component for covering magnetic particles produced in cells of a magnetic bacterium.

The magA gene described above has been found, isolated, and purified from a magnetic bacterium AMB-1 (FERM P-13282) as follows.

The magnetic bacterium AMB-1 was subjected to site-nonspecific mutagenesis in genome by introducing a transposon Tn5 as a transposable gene having a drug resistance factor (Km), and a mutant deficient in magnetic fine particle-producing function was prepared. Subsequently, a bacterial strain without any magnetic response was separated by using the drug resistance factor (Km) as an index, and the genome was extracted from the mutant in accordance with a method described in *Current Protocols in Molecular Biology*. After digestion with EcoRI, a gene fragment containing the magA gene was isolated by Southern hybridization by using an index of hybrid formation with the transposon Tn5, and purified by cloning into pUC19. As a result of gene analysis, the magA gene of 1.3 kb was obtained.

magA protein

A promoter sequence is adjacent to a sequence of the magA gene at an upstream position. The protein has its amino acid sequence as depicted in SEQ ID NO: 2 in Sequence Listing described below (depicted together with the base sequence), including a hydrophilic region in a range of 1st to 6th amino acid residues as counted from the N-terminal, a hydrophobic region in a range of following 7th to 380th amino acid residues, and the second hydrophilic region in a range of following 381th to 434th amino acid residues. The long hydrophobic region at the middle is a membrane binding site, and the hydrophilic regions at the both ends are in a state of being exposed out of the membrane. In detail, the hydrophobic region includes short hydrophilic portions at about 4 places. It is assumed that these portions are partially exposed out of the membrane.

This protein was isolated and purified as follows. The magnetic bacterium AMB-1 was cultivated until a stationary phase, bacterial cells were collected by centrifugation, and then cells were disrupted by using French Press. Magnetic particles were extracted and purified from the disrupted preparation by using a samarium cobalt magnet, followed by agitation for 2 hours in a 1% Tryton-10 mM Tris buffer to separate the magnetic particles from the membrane. As a result of electrophoresis (SDS-PAGE) for proteins included in the extracted preparation treated as described above, a band was confirmed at a position of 46.8 kDa as known as a molecular weight of a protein encoded by the magA gene.

As a result of search for homology with respect to the magA protein, high homology was presented with a protein which is responsible for the potassium ion efflux mechanism of *Escherichia coli*. Thus the MagA protein is considered to participate in efflux of cations. Accordingly, the magA gene was expressed in *Escherichia coli*, and inverted membrane liposomes were prepared after removing outer cell membrane. The efflux phenomenon of iron ion from the liposome was observed by using iron labeled with a radioisotope. As a result, it was found that the magA protein conducted discharge of iron ion.

The magA protein is encoded by the aforementioned magA gene, and, more generally, it is encoded by a DNA sequence fusing a base sequence represented by SEQ ID NO: 3 depicted in Sequence Listing.

Taking notice of the fact that the hydrophobic region of the magA protein has a function to bind the protein to the organic membrane of the magnetic particles, and that the hydrophobic regions at the both ends are exposed out of the organic membrane, the present inventors have found that when a DNA sequence coding for another useful protein is fused to the hydrophilic region, an obtained fusion DNA sequence produces the useful protein in the magnetic bacterium in a state of being bound to the organic membrane of the magnetic particles.

magA gene fragment

Thus according to a second aspect of the present invention, there is provided a magA gene fragment comprising a DNA sequence represented by a base sequence coding for a hydrophobic region in the amino acid sequence of a MagA protein bound to an organic membrane for covering magnetic particles produced in cells of a magnetic bacterium AMB-1, the hydrophobic region being a region of 7th to 380th amino acid residues shown in SEQ ID NO: 2 defined in Sequence Listing.

The magA gene fragment is useful as a fixing means for producing a fusion protein in a state of being bound to the organic membrane.

The magA gene fragment essentially contains the aforementioned hydrophobic region. However, all or a part of the base sequence existing in the magA gene may be present at the 3'-terminal side or the 5'-terminal side of the hydrophobic region.

Fusion DNA sequence

According to a third aspect of the present invention, there is provided a fusion DNA sequence comprising (a) the magA gene fragment, and (b) one or two DNA sequences coding for one or two useful proteins fused to one or both ends of the magA gene fragment.

The one or two DNA sequences coding for the one or two useful proteins may be fused to any one of the ends or both of the ends on the 3'-terminal side and the 5'-terminal side of the magA gene fragment. When fused to the both ends, the DNA sequence to be introduced into the 3'-terminal and the DNA sequence to be introduced into the 5'-terminal may code for an identical protein, or may code for different proteins. The advantage of fusion to the both ends is obtained in the following cases.

1) When a DNA sequence coding for an identical protein is introduced into the both ends, the amount of the protein immobilized on the magnetic particles can be increased.

2) When DNA sequences coding for a complex system comprising two serial enzymes or proteins of an enzyme and a coenzyme-reproducing enzyme are introduced into the 5'-terminal and the 3'-terminal, the reaction of the enzyme system can proceed quickly.

3) When DNA sequences coding for proteins to form subunits are introduced into the 5'-terminal and the 3'-terminal, the subunits can be formed quickly and completely.

The position at which the DNA sequence coding for the aforementioned useful protein is fused to the magA gene fragment is not limited provided that a base sequence produced at a fusion site is suitable for amino acid synthesis. The DNA sequence coding for the useful protein may be introduced in a configuration close to the DNA sequence coding for the hydrophobic region. The DNA sequence coding for the hydrophilic region may be party present between the DNA sequence coding for the hydrophobic region and the DNA sequence coding for the useful protein.

An artificially elongated DNA sequence may exist at one or both ends of the magA gene fragment so that a convenient restriction enzyme cleavage site is formed. Especially, since the hydrophilic region on the 5'-terminal side is short, all of it may exist, or this portion may be optionally elongated. The restriction enzyme cleavage site on the 5'-terminal side useful as a site for inserting a DNA sequence coding for an objective useful protein includes a ScaI cleavage site introduced into the magA gene. The restriction enzyme cleavage site on the 3'-terminal side includes a SphI cleavage site and a DraIII cleavage site. The SphI cleavage site and the DraIII cleavage site are located in the hydrophilic region deviating toward the downstream side a little distant from the hydrophobic region of the magA gene, and thus they are one of convenient sites respectively.

Recombinant plasmid

According to a fourth aspect of the present invention, there is provided a recombinant plasmid used for expressing the aforementioned fusion DNA sequence.

Namely, the present invention provides a recombinant plasmid comprising the aforementioned fusion DNA sequence.

The recombinant plasmid is obtained by introducing a fusion DNA sequence comprising the magA gene fragment and a DNA sequence coding for an objective protein into a suitable vector plasmid by means of a known method.

Those belonging to families of, for example, pRK415 and pKT230 may be used as a vector to be used for preparing the recombinant plasmid. A gene is incorporated into a selected vector. The order of incorporation of genes, and restriction enzymes to be used are determined so that they are most efficient for the vector, and that the genes are aligned in an objective orientation. After determination of the procedure for introducing genes, DNA is digested with a restriction enzyme. An objective gene fragment to be introduced is separated by conducting electrophoresis. After that, ligation is performed by using ligase to ligate DNA. If portions to be ligated of gene fragments are not fitted to one another, end portions are treated and blunt-ended, followed by ligation. All of restriction enzymes, ligase, and enzymes for forming blunt ends to be used may be those commercially available. Finally, a restriction enzyme digestion pattern is confirmed to know whether or not an objective plasmid is formed.

In this aspect, the type of the gene coding for another protein to be fused to the magA gene is not specifically limited.

Transformed magnetic bacterium

According to a fifth aspect of the present invention, there is provided a magnetic bacterium transformed with the aforementioned recombinant plasmid.

The magnetic bacterium may be transformed with the plasmid in accordance with a known method. The magnetic bacterium to be used as a host includes, for example, microorganisms belonging to the genus Magnetospirillum (for example, bacterial strains AMB-1 (FERM P-13282), MS-1 (IFO 15272, ATCC 31632, DSM 3856), MSR-1 (IFO 15272, DSM 6361)), and microorganisms belonging to the genus Desulfovibrio (for example, bacterial strain RS-1 (FERM P-13283)).

The magnetic particles having the objective useful protein are produced in cells by cultivating the magnetic bacterium thus obtained under a suitable condition. Specifically, the objective protein is obtained in a state of being fused to the membrane-bound protein encoded by the magA gene fragment, in a state of being bound to the organic membrane for covering the magnetic particles.

The protein-bound magnetic particles are especially useful when the protein is a functional protein, because the magnetic particles can be moved to a desired place by using a magnetic force, and the function possessed by the protein can be performed at the place.

Functional protein-bound magnetic particles

Thus, according to a sixth aspect of the present invention, there is provided functional protein-bound magnetic particles comprising magnetic particles, and a fusion protein containing one or two functional proteins encoded by the aforementioned fusion DNA sequence (provided that said useful proteins is functional proteins) bound to an organic membrane for covering surfaces of the magnetic particles.

Method for producing protein-bound magnetic particles

According to a seventh aspect of the present invention, there is provided a method for producing the aforementioned useful protein-bound magnetic particles, comprising the steps of cultivating a magnetic bacterium transformed with a plasmid containing the aforementioned fusion DNA sequence to express the aforementioned fusion DNA sequence and to produce the fusion protein containing a useful protein in cells in a state of being bound to an organic membrane for covering the magnetic particles.

The useful protein-bound magnetic particles can be easily collected by utilizing a magnetic force after disrupting or lysing cells of the magnetic bacterium grown by cultivation in accordance with an conventional method.

There is no limitation on the gene coding for the useful protein fused to the magA gene fragment according to the present invention, as well as the protein expressed thereby. In the case of the use for a purpose of medicine or industries utilizing fermentation, a protein having a certain function, for example, a biological activity, will be used. However, there is no limitation thereto. The present invention can be utilized to produce proteins which are difficult to be separated and obtained by using conventional methods. Namely, such a protein can be produced on the magnetic particles in a form of fusion protein, separated easily magnetically, and collected.

Among the useful proteins, the functional protein includes, for example, antigens, antibodies, immuno-related proteins such as Protein A, proteins having binding ability such as lectin and avidin, coenzymes, and enzymes such as hydrolases, oxidoreductases, isomerases, transferases, elimination enzymes, and restriction enzymes.

The method for producing useful proteins described above is useful as a method for producing such proteins when the proteins are difficult to be obtained in a pure form in accordance with conventional production methods, even when the proteins are useful proteins having no functionality. In this aspect, the useful protein is obtained in a state of being bound to the magnetic particles, however, it can be easily separated and purified from other cellular components in accordance with a magnetic method using a magnet or the like in the method described above.

Applicability

The present invention has applicability exemplified as follows.

1) Enzyme-bound carrier

In general, all enzymes which are ideally considered to work in a site-specific manner are worth while to be expressed on the surface of the magnetic particles. For example, when it is intended to perform an enzyme reaction locally in a reaction system of a biochemical reaction, magnetic particles on which the enzyme is expressed are useful. When it is intended to administrate an enzyme specifically to an organ in a disease of a certain enzyme system, it is possible to treat the disease by magnetically navigating the enzyme expressed on surface of magnetic particles.

2) DNA carrier

When a gene of a protein having an ability to bind to DNA or RNA, for example a protein such as a repressor, is fused to a magA gene fragment, and immobilized on magnetic particles according to the present invention, the magnetic particles can be used as a carrier to transport the gene. The protein such as a repressor has a property to lose its binding force in the presence of a specified substance. Therefore, The gene can be transported by utilizing this phenomenon. The repressor protein includes, for example, LacI. LacI is a protein which controls gene expression of lactose-decomposing enzyme, which is a repressor that suppresses transcription of the gene by being bound to a downstream region of a promoter. LacI loses its ability to bind to DNA as a result of binding to a chemical substance such as lactose and IPTG. Namely, there is a system in which expression occurs when a substrate to be decomposed is present. There is a specic DNA domain to which LacI binds. LacI can bind to a gene into which the DNA domain has been incorporated.

For example, LacI binds to a gene into which the DNA domain has been incorporated, by expressing LacI on the surface of the magnetic particles. On the other hand, LacI loses its ability to bind to DNA by a substance, known as IPTG. By using these phenomena, DNA can be magnetically transported from a particular place, and DNA can be liberated by addition of IPTG. Thus the gene can be transported to a desired place.

Therefore, the magnetic particles of the present invention are expected to be applied as carriers for transporting genes in genetic therapy. For example, at present, therapeutic methods are being diligently studied in which antisense RNA produced from a complementary chain of an objective gene is expressed to suppress expression of the objective gene by forming an RNA hybrid. The present invention can be used as a means for carrying DNA which serves to express the antisense RNA.

Further, a protein having a property to bind to a metal is expressed on the surface of the magnetic particles, and it can be used to recover or detect the metal. Recovery and detection may be performed by magnetic recovery.

3) Protein production system

In general, proteins which are said to be difficult in separation and purification can be easily separated and purified by expressing them as a fusion protein with the MagA protein on the magnetic particles. Because, the protein expressed on the surface of the magnetic particles can be easily recovered finally by using a magnetic force. Considering the high dispersibility of the magnetic particles obtained from the magnetic bacterium, many proteins may exist which can be used in a state of being immobilized on the magnetic particles. For example, enzymes for alcohol fermentation can be sufficiently used even in a state of being bound to the magnetic particles if they keep enzyme activities.

EXAMPLES

Example 1

I. Preparation of Recombinant Plasmids

In order to express a firefly luciferase gene (luc gene, produced by Toyo Ink) in a magnetic bacterium, and produce a luminescent protein encoded by the gene on an organic membrane for covering magnetic particles, a plasmid pKML ligated with a magA-luc fusion gene, and a plasmid pKPL ligated with only the luc gene without containing any magA gene were prepared in accordance with a method shown in FIG. 1.

(1) A plasmid pRK415 having a tetracycline resistance gene and capable of gene introduction into a magnetic bacterium AMB-1 through conjugative transfer (N. T. Neen, S. Tamaki, D. Kobayashi, and D. Trallinger, 1988, *Gene,* 70: 191–197) was used as a vector. The luc gene was incorporated into pRK415 to prepare a plasmid pKLC. The plasmid pKLC was digested at a BamHI existing at an upstream portion of the luc gene, and blunt-ended by using Blunting Kit (produced by Takara Shuzo Co., Ltd.).

Figure 2:
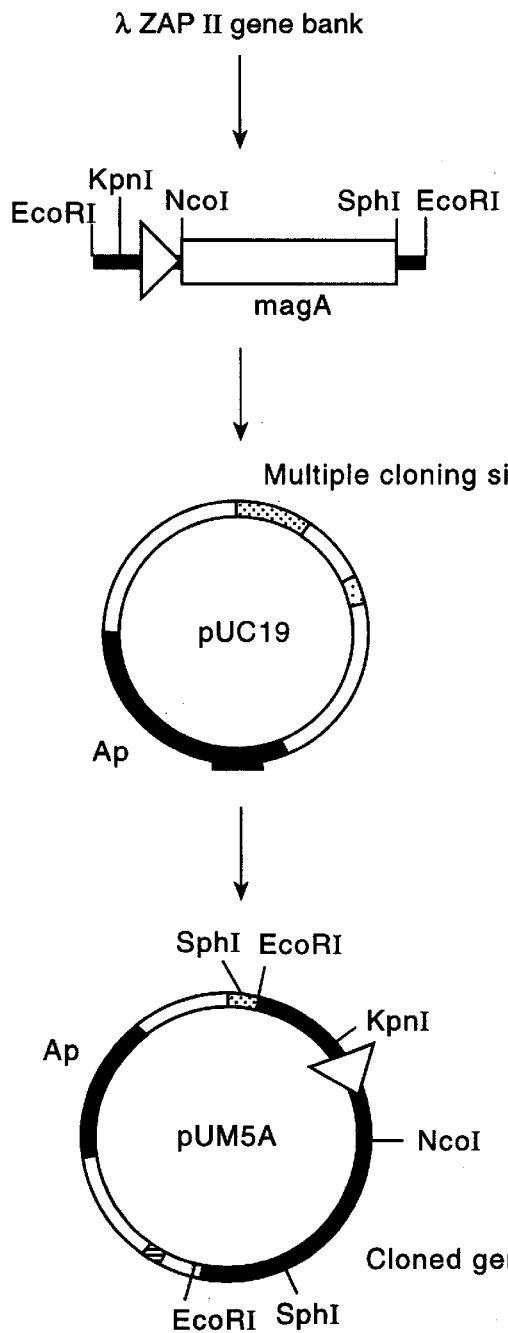
FIG. 2 is an explanatory view for a method for preparing a plasmid pUM5A prepared in Example 1.

(2) Chromosome of AMB-1 was digested with EcoRI, and randomly incorporated into λZAPII, a λDNA, to prepare a λZAPII gene bank. The gene bank was prepared in the form of plaques by packaging genes into phage particles, followed by infection to *Escherichia coli*. pUM5A was obtained by cloning 2.6 kbp of an EcoRI gene fragment containing the magA gene separated from the λZAPII gene bank into pUC19 (FIG. 2). Plaque Southern hybridization was performed upon the separation.

Next, the magA gene was digested at a SphI of the plasmid pUM5A. A magA gene fragment was separated, blunt-ended in the same manner, and ligated with the plasmid pKLC to prepare the plasmid pKML. Thus the luc gene can be translated without deviating from a reading frame of magA to produce a fusion protein.

(3) Only the sequence of a promoter separated by digestion with EcoRI and NcoI from the plasmid pUM5A was ligated with the plasmid pKLC having been blunt-ended in the same manner, and the plasmid pKPL was thereby prepared.

Figure 3:
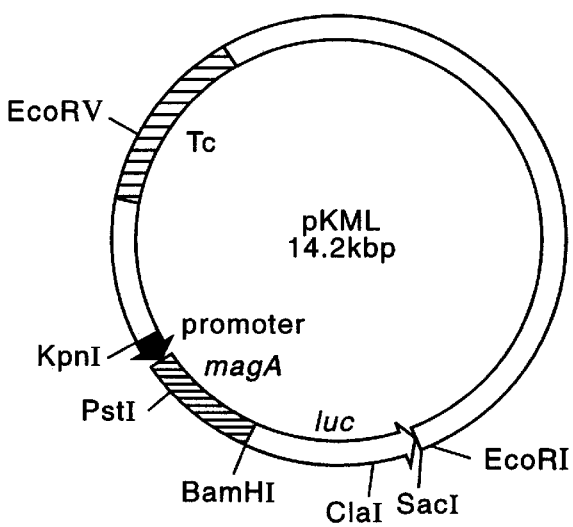
FIG. 3 is a map of restriction enzyme cleavage sites of the plasmid pKML.

Two types were prepared in accordance with the operation described above, namely the plasmid pKPL with only the promoter region ligated with the luc gene, and pKML with the ligated magA-luc fusion gene. A map of restriction enzyme cleavage sites of pKML is shown in FIG. 3.

II. Preparation of Transconjugants

Next, the two recombinant plasmids obtained in I were introduced into a wild strain AMB-1 by means of conjugative transfer to prepare transconjugants. *E. coli* S17-1, which was used as a donor in the conjugative transfer, had a tra gene. Thus the conjugative transfer could be performed without using any helper plasmid. Cells of the magnetic bacterium in a mid-logarithmic or late-logarithmic phase cultivated in an MSGM medium (about $8 \times 10^7$ cells/ml) were used for the conjugative transfer. Colonies generated by introducing the plasmid on the previous day were scraped and suspended to give $10^9$ to $10^{10}$ cells/ml, which were used as donor cells. The bacteria were mixed in 1:50 (magnetic bacterium:*Escherichia coli*), spotted on an agar plate to perform mating. After 6 hours, spots were cut with a knife to recover bacterial cells by using about 5 ml of MSGM medium. This suspension was inoculated to an MSGM medium added with 2.5 μg/ml of tetracycline. Cultivation was performed at 25° C., and grown cells were used as transconjugants. In this procedure, *Escherichia coli* does not grow on the MSGM medium.

Next, magnetic particles were separated from the magnetic bacterium cultivated in the MSGM medium after the conjugative transfer. Cells of the magnetic bacterium were collected by centrifugation, subsequently washed twice with 10 mM Tris buffer, suspended at a concentration not to exceed a cell concentration of 0.1 g wet cell/ml, and sonicated at an output of 120 W for 30 seconds five times. A disrupted cell suspension was treated for 30 minutes with an Nd-Co magnet abutting against an outer wall surface of a vessel while cooling it in the vessel with ice, and thus the magnetic particles were separated from the suspension. Cell membrane components were separated by centrifuging the suspension at 5,000 G for 15 minutes, and cytoplasm components were separated by ultracentrifuge at 100,000 G for 1.5 hour.

The luciferase activity of each fraction of the magnetic particles, cell membrane, and cytoplasm was determined by using a Pica Gene luminescence kit (produced by Toyo Ink), and measuring the amount of luminescence with a luminometer. Thus the expression and the expression amount of the introduced luciferase gene were determined. Results are shown in Table 1.

TABLE 1

|  | pKPL | pKML |
|---|---|---|
| Cytoplasmic fraction | 351.8 | 9.4 |
| Cell membrane fraction | 26.2 | 129.9 |
| Magnetic fine particle fraction | 1.9 | 12.5 |

(unit: kilocounts/mg protein)

As shown in Table 1, the magnetic bacterium in which the pKPL gene with the luc gene ligated with only the sequence of the promoter region was introduced, had a high amount of luminescence of the cytoplasmic fraction, and had a low protein expression efficiency on the surface of the magnetic particles. On the contrary, the magnetic bacterium in which pKML ligated with the magA-luc fusion gene was introduced, provided high amounts of luminescence in the magnetic fine particle fraction and the cell membrane fraction. Namely, the magA fusion protein which is a protein capable of binding to the membrane was expressed also in the magnetic fine particle fraction, demonstrating the production and separation of the luc protein on the organic membrane for covering the magnetic particles.

Example 2

Figure 4:
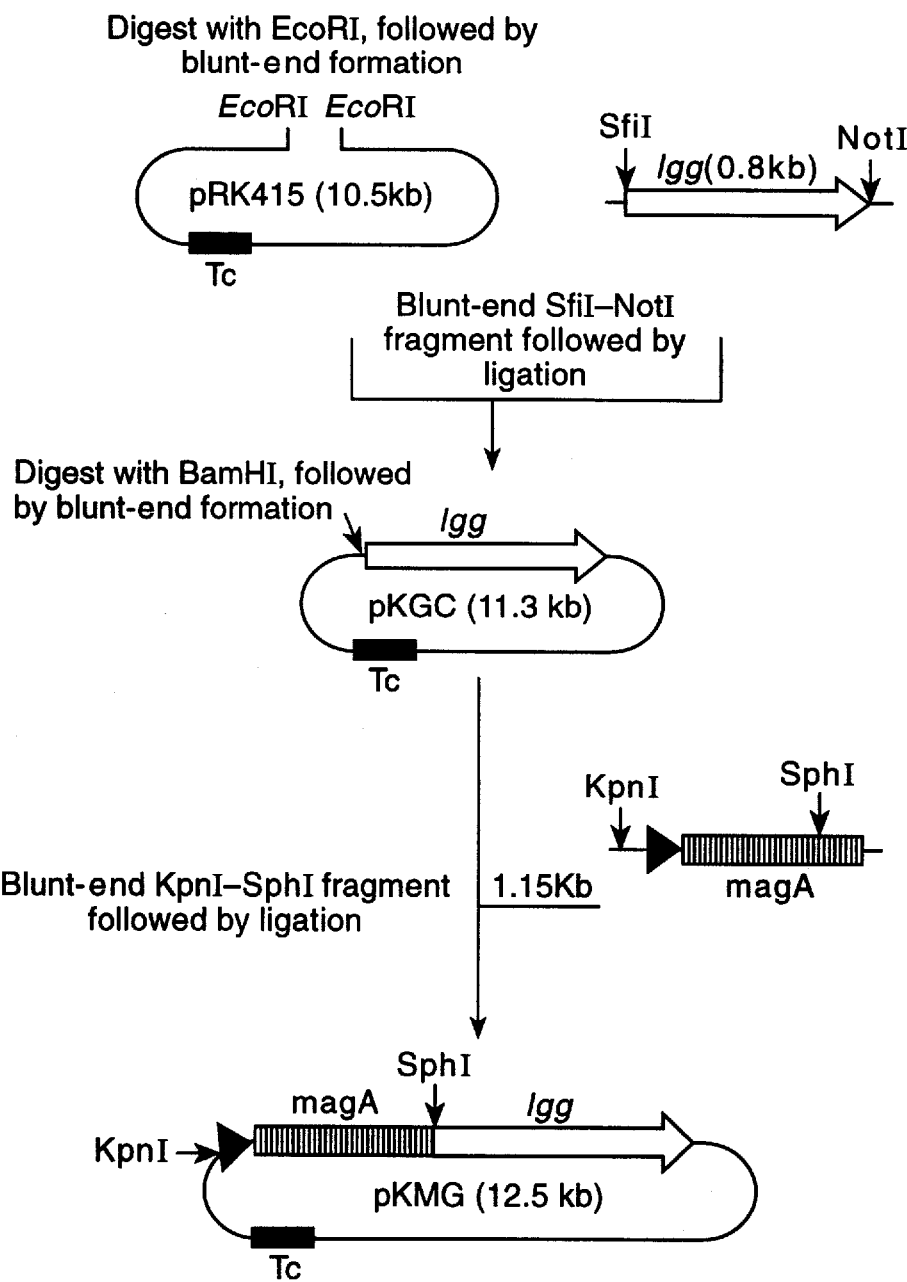
FIG. 4 is an explanatory view for a method for preparing a plasmid pKMG prepared in Example 2.

A gene coding for an antigen recognition site of an anti-rabbit IgG antibody (igg gene, produced by Pharmacia) was used. In order to produce an antibody protein encoded by the gene on the organic membrane containing as a major component phospholipid for covering the magnetic particles, a plasmid pKMG with a ligated magA-igg fusion gene was prepared in accordance with a method shown in FIG. 4.

That is, the plasmid pRK415 having a tetracycline resistance gene and capable of gene introduction into a magnetic bacterium AMB-1 through conjugative transfer was used as a vector. pRK415 was digested with EcoRI, and blunt-ended, into which the igg gene was incorporated to prepare a plasmid pKGC.

Next, chromosome of the magnetic bacterium AMB-1 was digested with EcoRI, and randomly incorporated into λZAPII (produced by STRATAGENE), a λDNA, to prepare a ZAPII gene bank. The gene bank was prepared in the form of plaques by packaging genes into phage particles, followed by infection to Escherichia coli. 2.6 kbp of an EcoRI gene fragment containing the magA gene separated from the λZAPII gene bank was cloned into pUC19 to prepare pUM5A.

Figure 5:
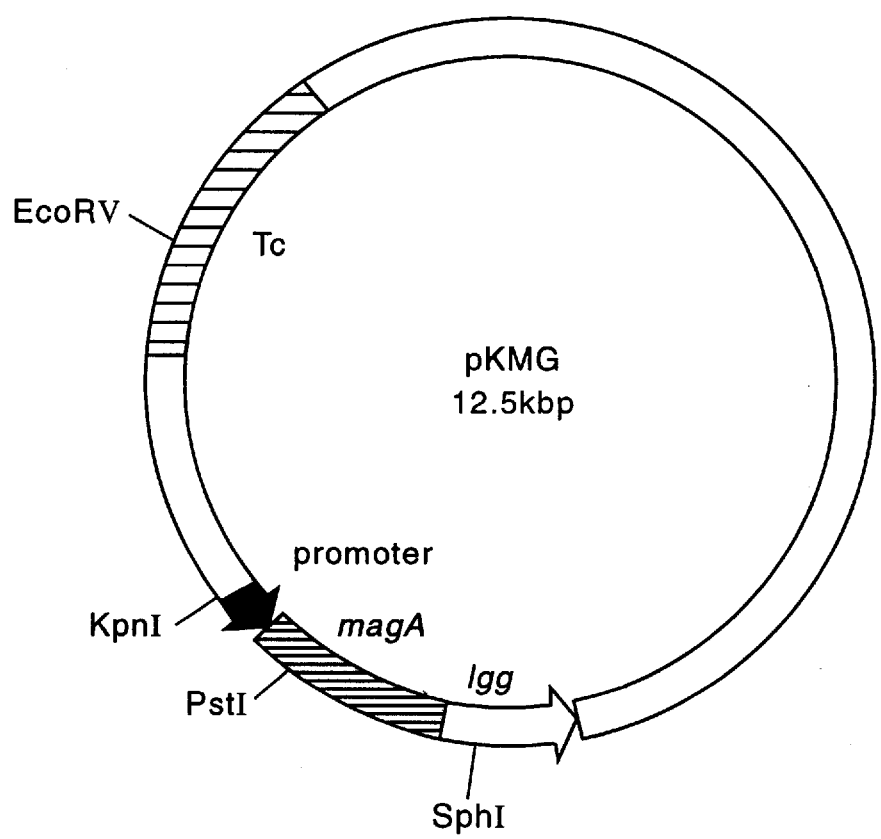
FIG. 5 is a map of restriction enzyme cleavage sites of the plasmid pKMG.

Next, the magA gene was digested at a SphI of the plasmid pUM5A. The magA gene was separated, blunt-ended, and ligated with the plasmid pKGC to prepare a plasmid pKMG. A map of restriction enzyme cleavage sites of pKMG is shown in FIG. 5.

This plasmid was introduced into a wild strain AMB-1 by means of conjugative transfer to prepare transconjugants. The transconjugants were cultivated, and cells were recovered and disrupted to recover the magnetic particles. The magnetic particles were used to perform immunoassay using rabbit IgG as an antigen. In the immunoassay, a sandwich method was used, in which an alkaline phosphatase-labeled anti-rabbit IgG antibody was used as a secondary antibody. For detection, the luminescence emitted by the reaction between alkaline phosphatase and AMPPD (Boehringer Mannheim Biochemica) was measured using a luminometer. As a result, the antibody could be detected. According to the experiment, the antibody bound to the magnetic particles of the transconjugants as a MagA fusion protein. Thus it was possible to produce the magnetic particles capable of being used for an antigen detecting system without any immobilizing operation.

Example 3

Figure 6:
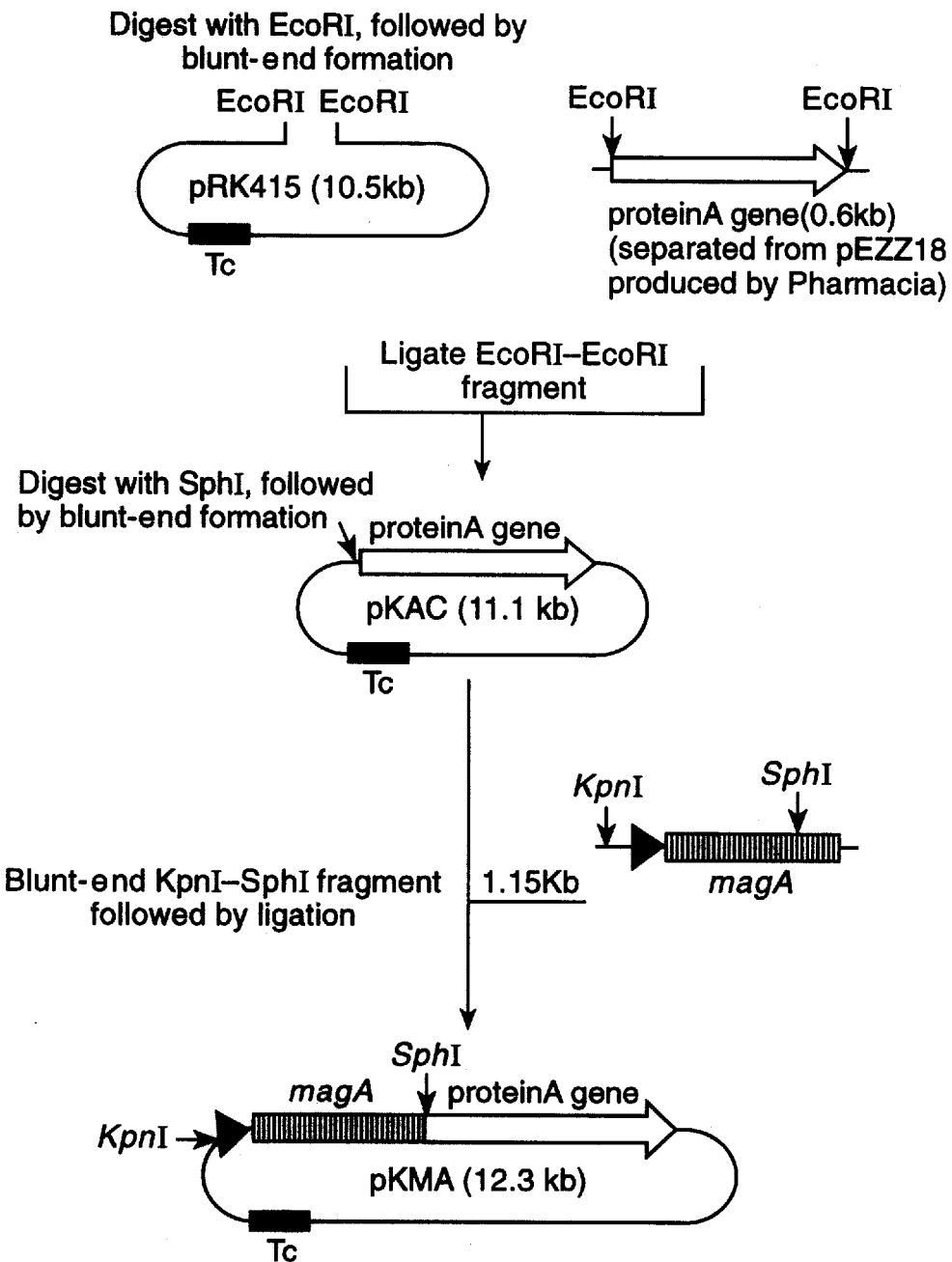
FIG. 6 is an explanatory view for a method for preparing a plasmid pKMA prepared in Example 3.

A Protein A gene (separated from pEZZ18 produced by Pharmacia) was used. In order to produce a protein encoded by the gene on the organic membrane containing as a major component phospholipid for covering the magnetic particles, a plasmid pKMA with a ligated magA-Protein A fusion gene was prepared in accordance with a method shown in FIG. 6.

Namely, the plasmid pRK415 having a tetracycline resistance gene and capable of gene introduction into a magnetic bacterium AMB-1 through conjugative transfer was used as a vector. pRK415 was digested with EcoRI, into which the Protein A gene was incorporated to prepare a plasmid pKAC.

Next, chromosome of the magnetic bacterium AMB-1 was digested with EcoRI, and randomly incorporated into λZAPII (produced by STRATAGENE), a λDNA, to prepare a λZAPII gene bank. The gene bank was prepared in the form of plaques by packaging genes into phage particles, followed by infection to Escherichia coli. 2.6 kbp of an EcoRI gene fragment containing the magA gene separated from the λZAPII gene bank was cloned into pUC19 to prepare pUM5A.

Figure 7:
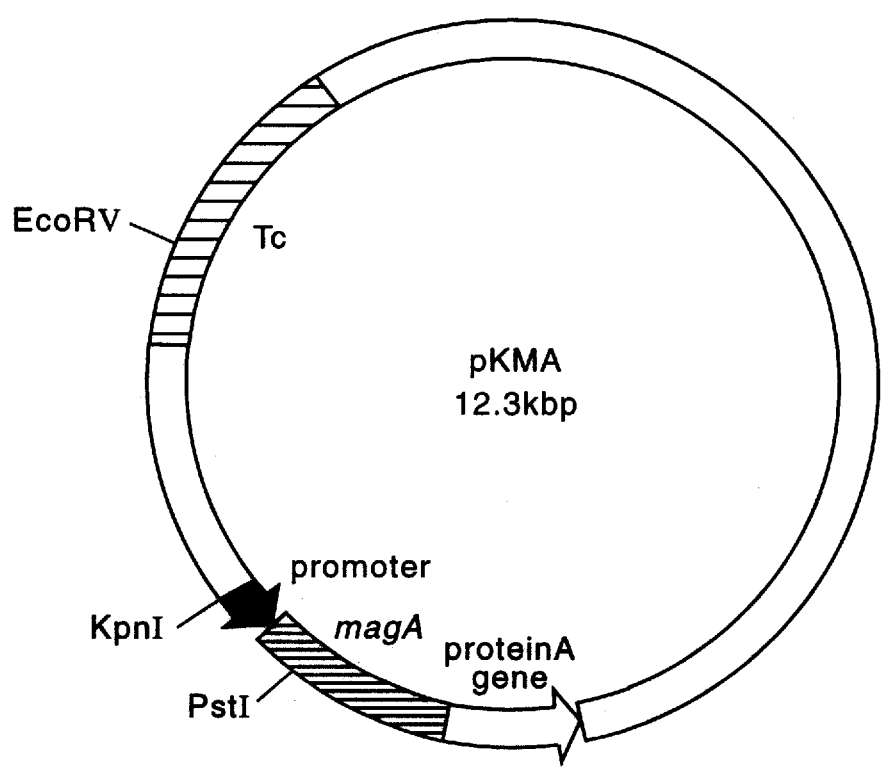
FIG. 7 is a map of restriction enzyme cleavage sites of the plasmid pKMA.

Next, the magA gene was digested at a SphI of the plasmid pUM5A. The magA gene was separated, and ligated with the blunt-ended plasmid pKAC to prepare a plasmid pKMA. A map of restriction enzyme cleavage sites of pKMA is shown in FIG. 7.

The plasmid was introduced into a wild strain AMB-1 by means of conjugative transfer to prepare transconjugants. The transconjugants were cultivated, and cells were recovered and disrupted to recover the magnetic particles. Taking notice of the binding ability of Protein A to IgG, the magnetic particles were mixed with anti-cedar pollen, anti-wheat, or anti-egg IgG. The mixed particles were washed, and the amount of immobilized antibody was measured. As a result, it was revealed that the immobilization was possible in approximately the same degree as that of a chemical binding method using SPDP having been hitherto used (Japanese Pre-examination Patent Publication (KOKAI) No. 5-209884). As a result of experiments for detecting antigens performed in the same manner as Example 1, all of the three antigens could be detected. Thus it was demonstrated that various IgG's could be readily and conveniently bound to the surface of the magnetic particles by using the MagA fusion protein of Protein A, and that antigens could be detected equivalently to the conventional chemical binding.

Example 4

Figure 8:
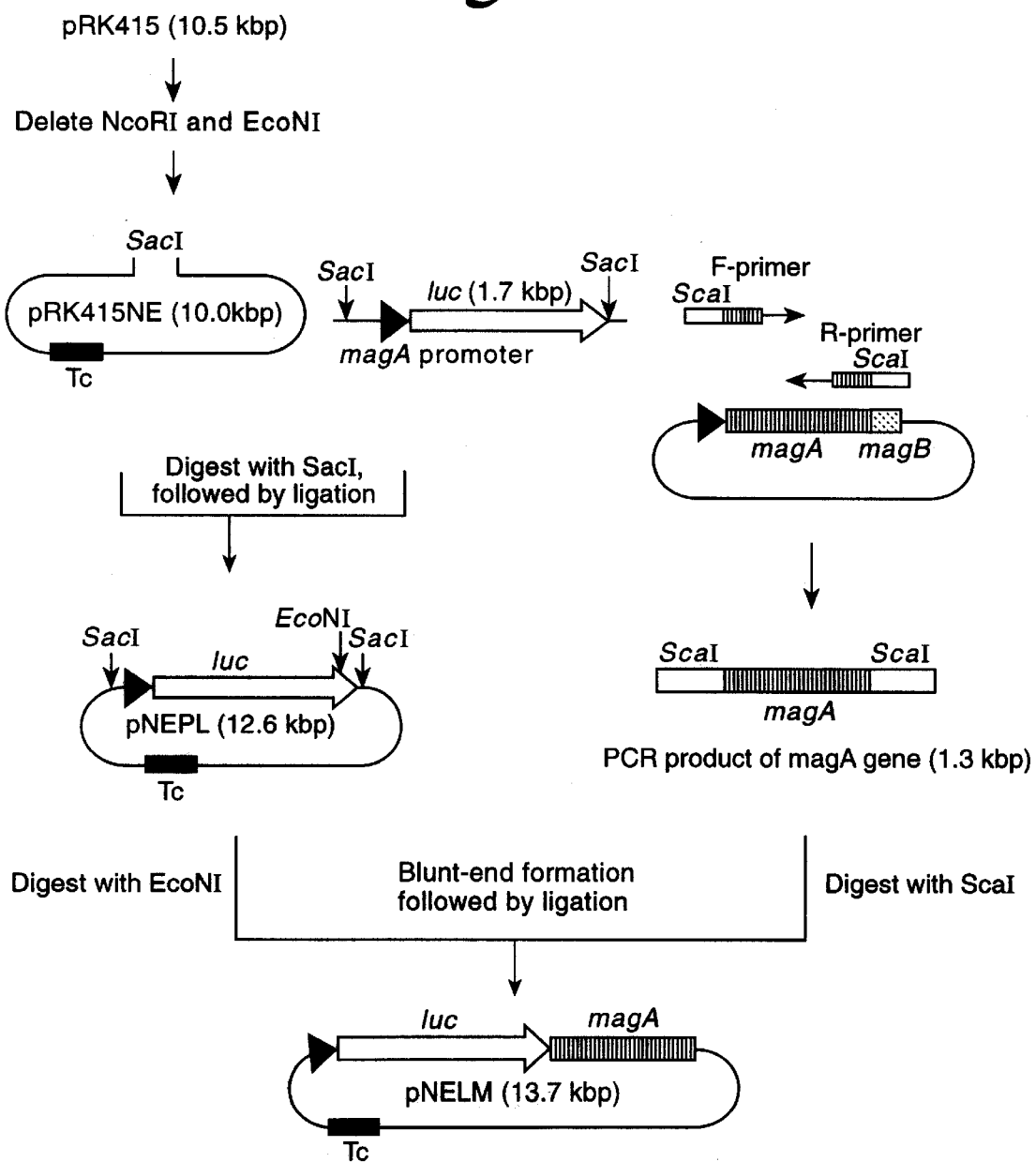
FIG. 8 is an explanatory view for a method for preparing a plasmid pNELM prepared in Example 4.

A firefly luciferase gene (luc gene) was introduced into a 5'-terminal side of the magA gene to prepare a plasmid pNELM containing a luc-magA fusion DNA sequence in accordance with a method shown in FIG. 8.

(1) The plasmid pRK415 having a tetracycline resistance gene and capable of gene introduction into a magnetic bacterium AMB-1 through conjugative transfer was used as a vector. An NcoI cleavage site and an EcoNI cleavage site of pRK415 were deleted by a blunt-ending treatment to prepare a plasmid pRK415NE. pRK415NE was digested with SacI to produce a plasmid pNEPL incorporated with a magA promoter-luc fusion gene.

Figure 9:
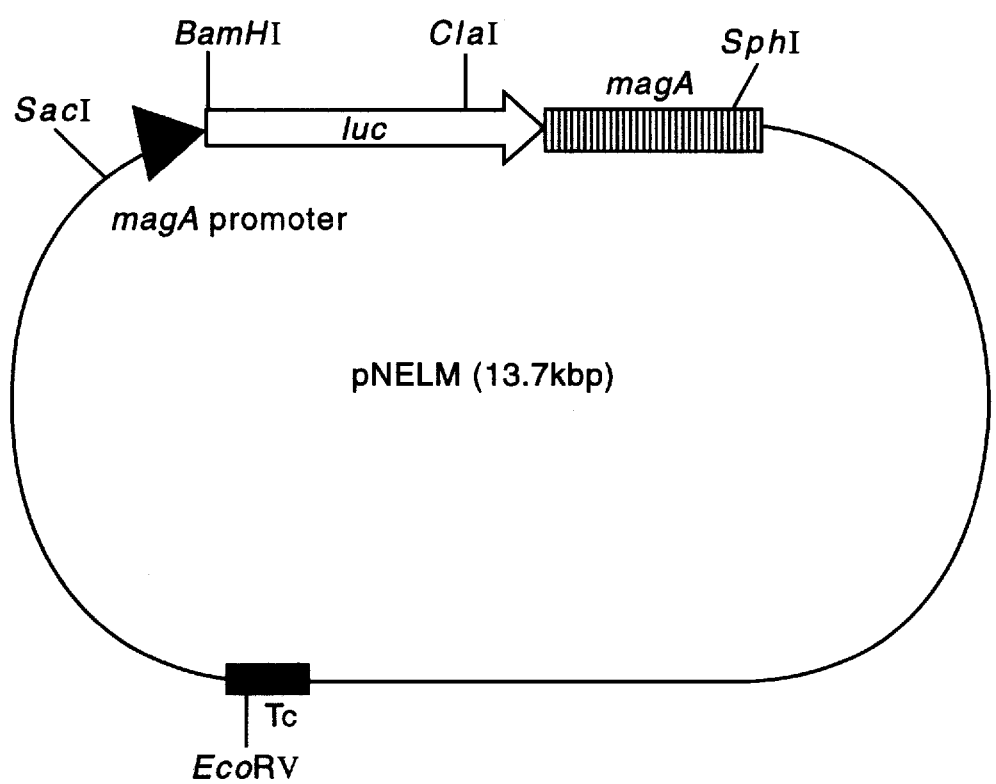
FIG. 9 is a map of restriction enzyme cleavage sites of the plasmid pNELM.

(2) Next, primers designed for a ScaI cleavage site were used with the plasmid pUM5A harboring the magA gene. The magA gene was amplified by PCR, digested with ScaI, and ligated with the plasmid pNEPL having been subjected to digestion with EcoNI followed by blunt end formation, to prepare a plasmid pNELM. A map of restriction enzyme cleavage sites of pNELM is shown in FIG. 9.

(3) The plasmid was introduced into a wild strain AMB-1 by means of conjugative transfer to prepare transconjugants. The transconjugants were cultivated and grown. Cells were recovered and disrupted to recover the magnetic particles using a magnet. The luciferase activity of the magnetic particles was determined by using a Pica Gene luminescence kit (produced by Toyo Ink), and measuring the amount of luminescence with a luminometer. Results are shown in Table 2.

TABLE 2

|  | pKML | PNELM |
| --- | --- | --- |
| Magnetic fine particle fraction | 24.5 | 45.8 |

(unit: kilocounts/µg protein)

Next, in order to confirm the exposing directions at the C-terminal and the N-terminal of the magA protein on the magnetic particles, the magnetic particles originating from transconjugants harboring the plasmid pKML ligated with the luc gene at the 3'-terminal of the magA gene, and the magnetic particles originating from transconjugants harboring the plasmid pNELM ligated with the luc gene at the 5'-terminal of the magA gene were used to perform an immunoassay using anti-luciferase IgG, and alkaline phosphatase-labeled anti-rabbit IgG. For detection, the luminescence emitted by the reaction between alkaline phosphatase and AMPPD (Boehringer Mannheim Biochemica) was measured by using a luminometer. Results are shown in Table 3.

TABLE 3

|  | AMB-1 | pKML | pNELM |
| --- | --- | --- | --- |
| Magnetic fine particle fraction | 37 | 290 | 195 |

(unit: kilocounts/mg protein)

According to this experiment, it was revealed that the N-terminal and the C-terminal of the MagA protein were exposed to the outside of the organic membrane for covering the magnetic particles. Therefore, it is possible to select the production as a fusion protein fused to the N-terminal of the MagA protein or the production as a fusion protein fused to the C-terminal, in accordance with the property of a functional protein.

Example 5

Figure 10:
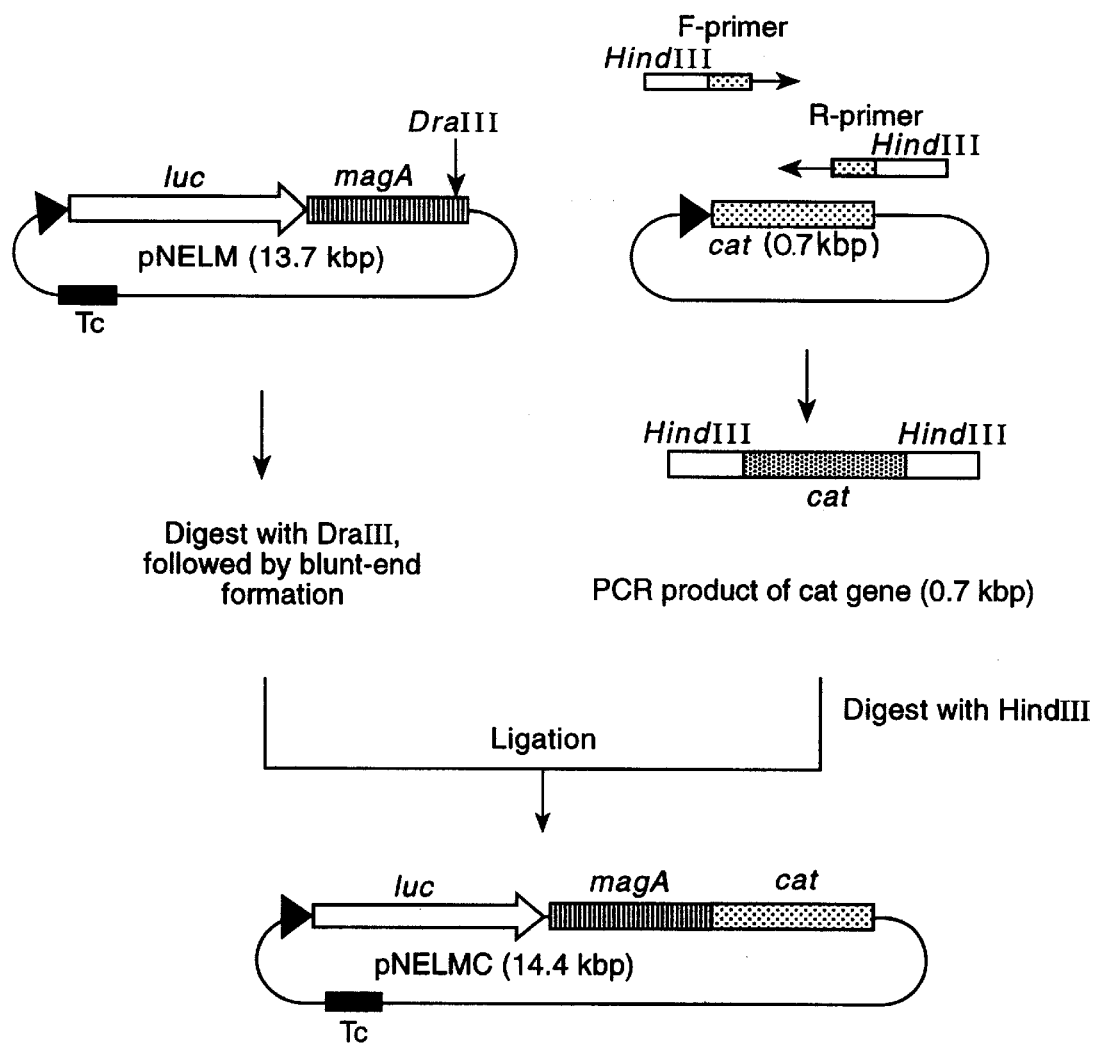
FIG. 10 is an explanatory view for a method for preparing pNELMC prepared in Example 5.

In order to simultaneously express a firefly luciferase gene and a chloramphenicol acetyl transferase (CAT) gene on the magnetic particles, a plasmid pNELMC as a gene containing a luc-magA-cat fusion DNA sequence was prepared in accordance with a method shown in FIG. 10.

Namely, the plasmid pRK415 having a tetracycline resistance gene and capable of gene introduction into a magnetic bacterium AMB-1 through conjugative transfer was used as a vector. The NcoI cleavage site and the EcoNI cleavage site of pRK415 were deleted by a blunt-ending treatment to prepare a plasmid pRK415NE. pRK415NE was digested with SacI to produce a plasmid pNEPL incorporated therein with a magA promoter-luc fusion gene.

Next, primers designed for a ScaI cleavage site were used with the plasmid pUM5A harboring the magA gene. The magA gene was amplified by PCR, digested with ScaI, and ligated with the plasmid pNEPL having been subjected to digestion with EcoNI, followed by blunt end formation, to prepare a plasmid pNELM.

Figure 11:
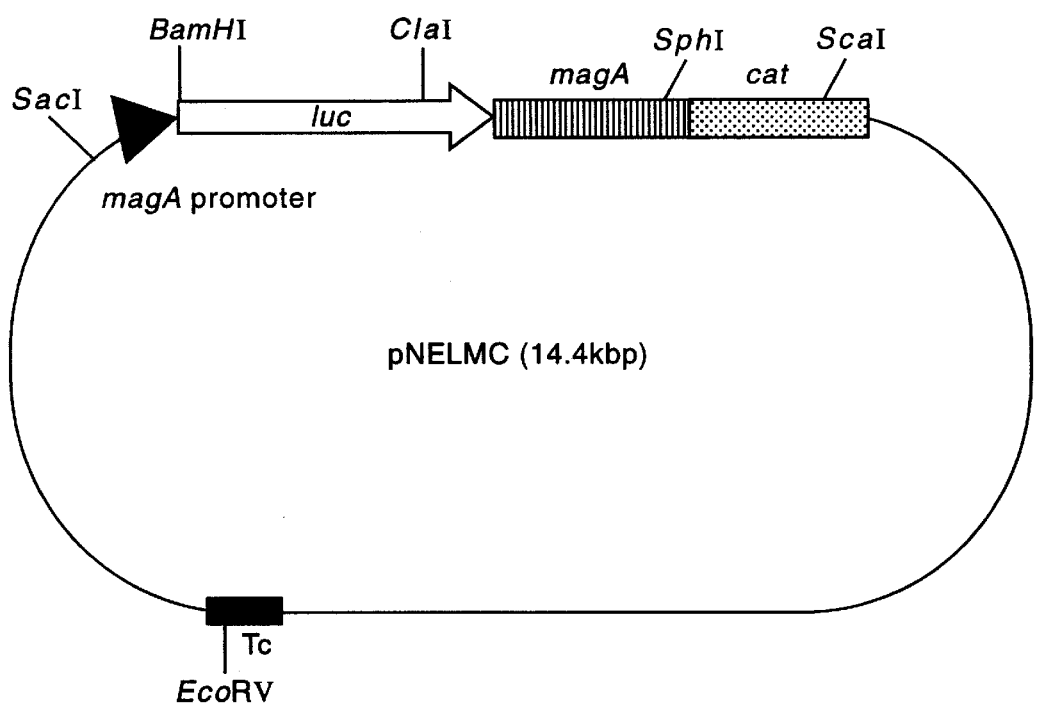
FIG. 11 is a map of restriction enzyme cleavage sites of the plasmid pNELMC.

Next, an SD sequence of the cat gene was eliminated, and primers designed for a ScaI cleavage site were used with the gene. The cat gene was amplified by PCR. It was ligated with the plasmid pNELM having been subjected to digestion with DraIII, followed by blunt end formation to prepare a plasmid pNELMC. A map of restriction enzyme cleavage sites of pNELMC is shown in FIG. 11.

This plasmid was introduced into a wild strain AMB-1 by means of conjugative transfer to prepare transconjugants. The transconjugants were cultivated and grown. Cells were recovered and disrupted to recover the magnetic particles using a magnet. The luciferase activity of the magnetic particles was determined by using a PICA GENE luminescence kit (produced by Toyo Ink), and measuring the amount of luminescence with a luminometer. As a result, a luciferase activity equivalent to that of pNELM was presented.

Next, as a result of CAT assay for the magnetic particles, the CAT activity was detected. The CAT assay was performed by detecting acetylated chloramphenicol produced by the reaction between chloramphenicol acetyl transferase and chloramphenicol by means of thin layer chromatography. As a result, each of the proteins bound to the both ends of the magA gene protein exhibited an activity equivalent to that obtained in the case of binding of each of the proteins singly. According to this experiment, it was possible to achieve simultaneous expression on the magnetic particles by constructing a fusion gene with genes coding for proteins having different functions ligated at the both ends of the magA gene protein. Thus the magnetic particles having a number of functions could be produced.

What is claimed is:

1. A fusion protein comprising:
    (a) a fragment of the magA gene product, the fragment comprising the amino acid sequence shown as residues 7–380 of SEQ ID NO: 2,
    (b) the amino acid sequence of a first protein of interest, and (c) optionally, the amino acid sequence of a second protein of interest;

wherein the first and optional second proteins of interest are the same or different, and wherein the first and optional second proteins of interest are joined to the N- or C-terminal of the fragment of the magA gene product.

2. A protein-bound magnetic particle comprising a magnetic particle, an organic membrane covering the surfgace of the magnetic particle, and a fusion protein according to claim 1 bound to the organic membrane.

3. A protein-bound magnetic particle according to claim 2, wherein either or both of the first and second proteins of interest is independently selected from the group consisting of an immunoglobulin, a binding protein, and an enzyme.

4. A DNA molecule encoding a fusion protein according to claim 1.

5. A plasmid comprising the nucleotide sequence of a DNA molecule according to claim 4.

6. A transformed host magnetic bacterium comprising a plasmid according to claim 5.

7. A transformed host magnetic bacterium according to claim 6, wherein the bacterium belongs to the species Magnetospirillum or Desulfovibrio.

8. A process for producing a protein-bound magnetic particle comprising a magnetic particle, an organic membrane covering the surface of the magnetic particle, and a fusion protein, the process comprising cultivating a transformed host magnetic bacterium according to claim 6 under conditions suitable to effect expression of the DNA molecule contained in the plasmid and to effect synthesis of the protein-bound magnetic particle by the transformed host magnetic bacterium.

9. A process according to claim 8, further comprising recovering the protein-bound magnetic particle by magnetic separation.

10. A fusion protein comprising:

(a) a fragment of the magA gene product, the fragment comprising the amino acid sequence shown as residues 7–380 of SEQ ID NO: 2, and (b) the amino acid sequence of a protein of interest selected from the group consisting of an immunoglobulin, a binding protein, and an enzyme;

wherein the protein of interest is joined to the N- or C-terminal of the fragment of the magA gene product.

11. A protein-bound magnetic particle comprising a magnetic particle, an organic membrane covering the surface of the magnetic particle, and a fusion protein according to claim 10 bound to the organic membrane.

12. A DNA molecule encoding a fusion protein according to claim 10.

13. A plasmid comprising the nucleotide sequence of a DNA molecule according to claim 12.

14. A transformed host magnetic bacterium comprising a plasmid according to claim 13.

15. A transformed host magnetic bacterium according to claim 14, wherein the bacterium belongs to the species Magnetospirillum or Desulfovibrio.

16. A process for producing a protein-bound magnetic particle comprising a magnetic particle, an organic membrane covering the surface of the magnetic particle, and a fusion protein, the process comprising cultivating a transformed host magnetic bacterium according to claim 14 under conditions suitable to effect expression of the DNA molecule contained in the plasmid and to effect synthesis of the protein-bound magnetic particle by the transformed host magnetic bacterium.

17. A process according to claim 16, further comprising recovering the protein-bound magnetic particle by magnetic separation.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
    ( A ) LENGTH: 1302 base pairs
    ( B ) TYPE: nucleic acid
    ( C ) STRANDEDNESS: double
    ( D ) TOPOLOGY: linear ( i i ) MOLECULE TYPE: DNA (genomic)

( i x ) FEATURE:
    ( A ) NAME/KEY: CDS
    ( B ) LOCATION: 1..1302

( x i ) SEQUENCE DESCRIPTION: SEQ ID NO:1:

| ATG | GAA | CTG | CAT | CAT | CCC | GAA | CTG | ACC | TAT | GCC | GCC | ATC | GTC | GCC | CTG | 48 |
| Met | Glu | Leu | His | His | Pro | Glu | Leu | Thr | Tyr | Ala | Ala | Ile | Val | Ala | Leu | |
| 1 | | | | 5 | | | | | 10 | | | | | 15 | | |

| GCC | GCC | GTG | CTG | TGC | GGC | GGG | ATG | ATG | ACG | CGC | CTG | AAG | CAG | CCG | GCC | 96 |
| Ala | Ala | Val | Leu | Cys | Gly | Gly | Met | Met | Thr | Arg | Leu | Lys | Gln | Pro | Ala | |
| | | | 20 | | | | | 25 | | | | | 30 | | | |

| GTC | GTC | GGC | TAC | ATC | CTG | GCG | GGG | GTG | GTG | CTG | GGA | CCC | AGC | GGC | TTC | 144 |
| Val | Val | Gly | Tyr | Ile | Leu | Ala | Gly | Val | Val | Leu | Gly | Pro | Ser | Gly | Phe | |
| | | 35 | | | | | 40 | | | | | 45 | | | | |

| GGG | CTG | GTG | AGC | AAC | CGC | GAC | GCC | GTG | GCC | ACC | CTG | GCC | GAG | TTC | GGC | 192 |
| Gly | Leu | Val | Ser | Asn | Arg | Asp | Ala | Val | Ala | Thr | Leu | Ala | Glu | Phe | Gly | |
| | 50 | | | | | 55 | | | | | 60 | | | | | |

| GTG | CTG | ATG | CTG | CTG | TTC | GTC | ATC | GGC | ATG | AAG | CTG | GAC | ATC | ATC | CGC | 240 |
| Val | Leu | Met | Leu | Leu | Phe | Val | Ile | Gly | Met | Lys | Leu | Asp | Ile | Ile | Arg | |
| 65 | | | | | 70 | | | | | 75 | | | | | 80 | |

| TTT | CTC | GAA | GTG | TGG | AAG | ACG | GCC | ATC | TTC | ACC | ACG | GTT | CTG | CAG | ATC | 288 |
| Phe | Leu | Glu | Val | Trp | Lys | Thr | Ala | Ile | Phe | Thr | Thr | Val | Leu | Gln | Ile | |
| | | | | 85 | | | | | 90 | | | | | 95 | | |

| GCC | GGC | AGC | GTG | GGC | ACG | GCC | CTG | CTG | CTG | CGT | CAC | GGC | CTG | GGC | TGG | 336 |
| Ala | Gly | Ser | Val | Gly | Thr | Ala | Leu | Leu | Leu | Arg | His | Gly | Leu | Gly | Trp | |
| | | | 100 | | | | | 105 | | | | | 110 | | | |

| AGC | CTG | GGG | CTG | GCG | GTG | GTG | CTG | GGC | TGT | GCC | GTG | GCG | GTG | TCG | TCC | 384 |
| Ser | Leu | Gly | Leu | Ala | Val | Val | Leu | Gly | Cys | Ala | Val | Ala | Val | Ser | Ser | |
| | | 115 | | | | | 120 | | | | | 125 | | | | |

| ACC | GCC | GTA | GTG | ATC | AAG | GTG | CTG | GAA | TCC | TCG | GAC | GAG | CTG | GAC | ACG | 432 |
| Thr | Ala | Val | Val | Ile | Lys | Val | Leu | Glu | Ser | Ser | Asp | Glu | Leu | Asp | Thr | |
| | 130 | | | | | 135 | | | | | 140 | | | | | |

| CCG | GTC | GGC | CGC | ACC | ACC | CTT | GGC | ATC | CTG | ATC | GCC | CAG | GAC | ATG | GCG | 480 |
| Pro | Val | Gly | Arg | Thr | Thr | Leu | Gly | Ile | Leu | Ile | Ala | Gln | Asp | Met | Ala | |
| 145 | | | | | 150 | | | | | 155 | | | | | 160 | |

| GTG | GTG | CCC | ATG | ATG | CTG | GTG | CTG | GAA | TCC | TTC | GAG | ACC | AAG | GCG | CTG | 528 |
| Val | Val | Pro | Met | Met | Leu | Val | Leu | Glu | Ser | Phe | Glu | Thr | Lys | Ala | Leu | |
| | | | | 165 | | | | | 170 | | | | | 175 | | |

| CTG | CCC | GCC | GAC | ATG | GCC | CGG | GTG | GTG | CTG | TCG | GTG | CTG | TTC | CTG | GTG | 576 |
| Leu | Pro | Ala | Asp | Met | Ala | Arg | Val | Val | Leu | Ser | Val | Leu | Phe | Leu | Val | |
| | | | 180 | | | | | 185 | | | | | 190 | | | |

| CTG | CTG | TTC | TGG | TGG | CTG | TCC | AAG | CGC | CGC | ATC | GAC | CTG | CCG | ATC | ACC | 624 |
| Leu | Leu | Phe | Trp | Trp | Leu | Ser | Lys | Arg | Arg | Ile | Asp | Leu | Pro | Ile | Thr | |
| | | 195 | | | | | 200 | | | | | 205 | | | | |

| GCC | CGG | CTT | TCC | CGC | GAT | TCT | GAC | CTT | GCC | ACC | CTG | TCG | ACC | CTG | GCC | 672 |
| Ala | Arg | Leu | Ser | Arg | Asp | Ser | Asp | Leu | Ala | Thr | Leu | Ser | Thr | Leu | Ala | |
| | 210 | | | | | 215 | | | | | 220 | | | | | |

| | | | | | | | | | | | | | | | | |
|---|---|---|---|---|---|---|---|---|---|---|---|---|---|---|---|---|
| TGG | TGT | TTC | GGC | ACC | GCC | GCC | ATC | TCC | GGC | GTG | CTG | GAC | TTG | TCG | CCG | 720 |
| Trp | Cys | Phe | Gly | Thr | Ala | Ala | Ile | Ser | Gly | Val | Leu | Asp | Leu | Ser | Pro | |
| 225 | | | | 230 | | | | | 235 | | | | | | 240 | |
| GCC | TAT | GGC | GCC | TTC | CTG | GGC | GGC | GTG | GTG | CTG | GGC | AAT | TCC | GCC | CAG | 768 |
| Ala | Tyr | Gly | Ala | Phe | Leu | Gly | Gly | Val | Val | Leu | Gly | Asn | Ser | Ala | Gln | |
| | | | | 245 | | | | | 250 | | | | | 255 | | |
| CGC | GAC | ATG | CTG | TTG | AAG | CGT | GCC | CAG | CCC | ATC | GGC | AGC | GTG | CTG | CTG | 816 |
| Arg | Asp | Met | Leu | Leu | Lys | Arg | Ala | Gln | Pro | Ile | Gly | Ser | Val | Leu | Leu | |
| | | | 260 | | | | | 265 | | | | | 270 | | | |
| ATG | GTG | TTC | TTC | CTG | TCC | ATC | GGG | CTG | CTG | CTC | GAC | TTC | AAG | TTC | ATC | 864 |
| Met | Val | Phe | Phe | Leu | Ser | Ile | Gly | Leu | Leu | Leu | Asp | Phe | Lys | Phe | Ile | |
| | | 275 | | | | | 280 | | | | | 285 | | | | |
| TGG | AAG | AAT | CTG | GGC | ACC | GTT | CTC | ACC | CTG | CTG | GCC | ATG | GTG | ACC | CTG | 912 |
| Trp | Lys | Asn | Leu | Gly | Thr | Val | Leu | Thr | Leu | Leu | Ala | Met | Val | Thr | Leu | |
| | 290 | | | | | 295 | | | | | 300 | | | | | |
| TTC | AAG | ACG | GCG | CTG | AAC | GTC | ACG | GCG | CTG | CGC | CTG | GCG | CGG | CAG | GAC | 960 |
| Phe | Lys | Thr | Ala | Leu | Asn | Val | Thr | Ala | Leu | Arg | Leu | Ala | Arg | Gln | Asp | |
| 305 | | | | | 310 | | | | | 315 | | | | | 320 | |
| TGG | CCC | AGC | GCC | TTC | CTG | GCC | GGC | GTG | GCC | CTG | GCC | CAG | ATC | GGC | GAG | 1008 |
| Trp | Pro | Ser | Ala | Phe | Leu | Ala | Gly | Val | Ala | Leu | Ala | Gln | Ile | Gly | Glu | |
| | | | | 325 | | | | | 330 | | | | | 335 | | |
| TTC | TCG | TTC | CTG | CTG | GCC | GAG | ACC | GGC | AAG | GCG | GTC | AAG | CTG | ATC | AGC | 1056 |
| Phe | Ser | Phe | Leu | Leu | Ala | Glu | Thr | Gly | Lys | Ala | Val | Lys | Leu | Ile | Ser | |
| | | | 340 | | | | | 345 | | | | | 350 | | | |
| GCC | CAG | GAG | ACC | AAG | CTG | GTG | GTG | GCG | GTC | ACC | GTG | CTG | TCC | CTG | GTG | 1104 |
| Ala | Gln | Glu | Thr | Lys | Leu | Val | Val | Ala | Val | Thr | Val | Leu | Ser | Leu | Val | |
| | | 355 | | | | | 360 | | | | | 365 | | | | |
| CTG | TCG | CCG | TTC | TGG | CTG | TTC | ACC | ATG | CGG | CGC | ATG | CAC | CGG | GTG | GCG | 1152 |
| Leu | Ser | Pro | Phe | Trp | Leu | Phe | Thr | Met | Arg | Arg | Met | His | Arg | Val | Ala | |
| | | 370 | | | | | 375 | | | | | 380 | | | | |
| GCG | GTG | CAT | GTC | CAT | TCG | TTC | CGC | GAT | CTG | GTC | ACG | CGG | CTG | TAT | GGC | 1200 |
| Ala | Val | His | Val | His | Ser | Phe | Arg | Asp | Leu | Val | Thr | Arg | Leu | Tyr | Gly | |
| 385 | | | | | 390 | | | | | 395 | | | | | 400 | |
| GAC | GAG | GCC | CGC | GCT | TTC | GCC | CGC | ACC | GCG | CGG | CGG | GCC | CGT | GTG | CTG | 1248 |
| Asp | Glu | Ala | Arg | Ala | Phe | Ala | Arg | Thr | Ala | Arg | Arg | Ala | Arg | Val | Leu | |
| | | | | 405 | | | | | 410 | | | | | 415 | | |
| GTG | CGG | CGT | GGT | TCC | TGG | AGG | GAT | GAC | CCC | AAT | GCC | GGA | CCT | GGC | TCT | 1296 |
| Val | Arg | Arg | Gly | Ser | Trp | Arg | Asp | Asp | Pro | Asn | Ala | Gly | Pro | Gly | Ser | |
| | | | 420 | | | | | 425 | | | | | 430 | | | |
| GGA | ATT | | | | | | | | | | | | | | | 1302 |
| Gly | Ile | | | | | | | | | | | | | | | |

(2) INFORMATION FOR SEQ ID NO:2:

(i) SEQUENCE CHARACTERISTICS:
        (A) LENGTH: 434 amino acids
        (B) TYPE: amino acid
        (D) TOPOLOGY: linear (ii) MOLECULE TYPE: protein (xi) SEQUENCE DESCRIPTION: SEQ ID NO:2:

| | | | | | | | | | | | | | | |
|---|---|---|---|---|---|---|---|---|---|---|---|---|---|---|
| Met | Glu | Leu | His | His | Pro | Glu | Leu | Thr | Tyr | Ala | Ala | Ile | Val | Ala | Leu |
| 1 | | | | 5 | | | | | 10 | | | | | 15 | |
| Ala | Ala | Val | Leu | Cys | Gly | Gly | Met | Met | Thr | Arg | Leu | Lys | Gln | Pro | Ala |
| | | | 20 | | | | | 25 | | | | | 30 | | |
| Val | Val | Gly | Tyr | Ile | Leu | Ala | Gly | Val | Val | Leu | Gly | Pro | Ser | Gly | Phe |
| | | 35 | | | | | 40 | | | | | 45 | | | |
| Gly | Leu | Val | Ser | Asn | Arg | Asp | Ala | Val | Ala | Thr | Leu | Ala | Glu | Phe | Gly |
| | 50 | | | | | 55 | | | | | 60 | | | | |
| Val | Leu | Met | Leu | Leu | Phe | Val | Ile | Gly | Met | Lys | Leu | Asp | Ile | Ile | Arg |

```
              65                      70                      75                      80
Phe  Leu  Glu  Val  Trp  Lys  Thr  Ala  Ile  Phe  Thr  Thr  Val  Leu  Gln  Ile
                         85                      90                      95
Ala  Gly  Ser  Val  Gly  Thr  Ala  Leu  Leu  Arg  His  Gly  Leu  Gly  Trp
              100                     105                     110
Ser  Leu  Gly  Leu  Ala  Val  Val  Leu  Gly  Cys  Ala  Val  Ala  Val  Ser  Ser
              115                     120                     125
Thr  Ala  Val  Val  Ile  Lys  Val  Leu  Glu  Ser  Ser  Asp  Glu  Leu  Asp  Thr
     130                     135                     140
Pro  Val  Gly  Arg  Thr  Thr  Leu  Gly  Ile  Leu  Ile  Ala  Gln  Asp  Met  Ala
145                     150                     155                     160
Val  Val  Pro  Met  Met  Leu  Val  Leu  Glu  Ser  Phe  Glu  Thr  Lys  Ala  Leu
                    165                     170                     175
Leu  Pro  Ala  Asp  Met  Ala  Arg  Val  Val  Leu  Ser  Val  Leu  Phe  Leu  Val
              180                     185                     190
Leu  Leu  Phe  Trp  Trp  Leu  Ser  Lys  Arg  Arg  Ile  Asp  Leu  Pro  Ile  Thr
              195                     200                     205
Ala  Arg  Leu  Ser  Arg  Asp  Ser  Asp  Leu  Ala  Thr  Leu  Ser  Thr  Leu  Ala
     210                     215                     220
Trp  Cys  Phe  Gly  Thr  Ala  Ala  Ile  Ser  Gly  Val  Leu  Asp  Leu  Ser  Pro
225                     230                     235                     240
Ala  Tyr  Gly  Ala  Phe  Leu  Gly  Gly  Val  Val  Leu  Gly  Asn  Ser  Ala  Gln
                    245                     250                     255
Arg  Asp  Met  Leu  Leu  Lys  Arg  Ala  Gln  Pro  Ile  Gly  Ser  Val  Leu  Leu
              260                     265                     270
Met  Val  Phe  Phe  Leu  Ser  Ile  Gly  Leu  Leu  Leu  Asp  Phe  Lys  Phe  Ile
          275                     280                     285
Trp  Lys  Asn  Leu  Gly  Thr  Val  Leu  Thr  Leu  Leu  Ala  Met  Val  Thr  Leu
     290                     295                     300
Phe  Lys  Thr  Ala  Leu  Asn  Val  Thr  Ala  Leu  Arg  Leu  Ala  Arg  Gln  Asp
305                     310                     315                     320
Trp  Pro  Ser  Ala  Phe  Leu  Ala  Gly  Val  Ala  Leu  Ala  Gln  Ile  Gly  Glu
                    325                     330                     335
Phe  Ser  Phe  Leu  Leu  Ala  Glu  Thr  Gly  Lys  Ala  Val  Lys  Leu  Ile  Ser
              340                     345                     350
Ala  Gln  Glu  Thr  Lys  Leu  Val  Val  Ala  Val  Thr  Val  Leu  Ser  Leu  Val
          355                     360                     365
Leu  Ser  Pro  Phe  Trp  Leu  Phe  Thr  Met  Arg  Arg  Met  His  Arg  Val  Ala
     370                     375                     380
Ala  Val  His  Val  His  Ser  Phe  Arg  Asp  Leu  Val  Thr  Arg  Leu  Tyr  Gly
385                     390                     395                     400
Asp  Glu  Ala  Arg  Ala  Phe  Ala  Arg  Thr  Ala  Arg  Arg  Ala  Arg  Val  Leu
              405                     410                     415
Val  Arg  Arg  Gly  Ser  Trp  Arg  Asp  Asp  Pro  Asn  Ala  Gly  Pro  Gly  Ser
              420                     425                     430
Gly  Ile
```

( 2 ) INFORMATION FOR SEQ ID NO:3:

( i ) SEQUENCE CHARACTERISTICS:
        ( A ) LENGTH: 1302 base pairs
        ( B ) TYPE: nucleic acid
        ( C ) STRANDEDNESS: double
        ( D ) TOPOLOGY: linear ( i i ) MOLECULE TYPE: DNA (genomic)

(xi) SEQUENCE DESCRIPTION: SEQ ID NO:3:

| | | | | | | |
|---|---|---|---|---|---|---|
| ATGGARYTNC | AYCAYCCNGA | RYTNACNTAY | GCNGCNATHG | TNGCNYTNGC | NGCNGTNYTN | 60 |
| TGYGGNGGNA | TGATGACNMG | NYTNAARCAR | CCNGCNGTNG | TNGGNTAYAT | HYTNGCNGGN | 120 |
| GTNGTNYTNG | GNCCNWSNGG | NTTYGGNYTN | GTNWSNAAYM | GNGAYGCNGT | NGCNACNYTN | 180 |
| GCNGARTTYG | GNGTNYTNAT | GYTNYTNTTY | GTNATHGGNA | TGAARYTNGA | YATHATHMGN | 240 |
| TTYYTNGARG | TNTGGAARAC | NGCNATHTTY | ACNACNGTNY | TNCARATHGC | NGGNWSNGTN | 300 |
| GGNACNGCNY | TNYTNYTNMG | NCAYGGNYTN | GGNTGGWSNY | TNGGNYTNGC | NGTNGTNYTN | 360 |
| GGNTGYGCNG | TNGCNGTNWS | NWSNACNGCN | GTNGTNATHA | ARGTNYTNGA | RWSNWSNGAY | 420 |
| GARYTNGAYA | CNCCNGTNGG | NMGNACNACN | YTNGGNATHY | TNATHGCNCA | RGAYATGGCN | 480 |
| GTNGTNCCNA | TGATGYTNGT | NYTNGARWSN | TTYGARACNA | ARGCNYTNYT | NCCNGCNGAY | 540 |
| ATGGCNMGNG | TNGTNYTNWS | NGTNYTNTTY | YTNGTNYTNY | TNTTYTGGTG | GYTNWSNAAR | 600 |
| MGNMGNATHG | AYYTNCCNAT | HACNGCNMGN | YTNWSNMGNG | AYWSNGAYYT | NGCNACNYTN | 660 |
| WSNACNYTNG | CNTGGTGYTT | YGGNACNGCN | GCNATHWSNG | GNGTNYTNGA | YYTNWSNCCN | 720 |
| GCNTAYGGNG | CNTTYYTNGG | NGGNGTNGTN | YTNGGNAAYW | SNGCNCARMG | NGAYATGYTN | 780 |
| YTNAARMGNG | CNCARCCNAT | HGGNWSNGTN | YTNYTNATGG | TNTTYTTYYT | NWSNATHGGN | 840 |
| YTNYTNYTNG | AYTTYAARTT | YATHTGGAAR | AAYYTNGGNA | CNGTNYTNAC | NYTNYTNGCN | 900 |
| ATGGTNACNY | TNTTYAARAC | NGCNYTNAAY | GTNACNGCNY | TNMGNYTNGC | NMGNCARGAY | 960 |
| TGGCCNWSNG | CNTTYYTNGC | NGGNGTNGCN | YTNGCNCARA | THGGNGARTT | YWSNTTYYTN | 1020 |
| YTNGCNGARA | CNGGNAARGC | NGTNAARYTN | ATHWSNGCNC | ARGARACNAA | RYTNGTNGTN | 1080 |
| GCNGTNACNG | TNYTNWSNYT | NGTNYTNWSN | CCNTTYTGGY | TNTTYACNAT | GMGNMGNATG | 1140 |
| CAYMGNGTNG | CNGCNGTNCA | YGTNCAYWSN | TTYMGNGAYY | TNGTNACNMG | NYTNTAYGGN | 1200 |
| GAYGARGCNM | GNGCNTTYGC | NMGNACNGCN | MGNMGNGCNM | GNGTNYTNGT | NMGNMGNGGN | 1260 |
| WSNTGGMGNG | AYGAYCCNAA | YGCNGGNCCN | GGNWSNGGNA | TH | | 1302 |